(12) United States Patent
Herold et al.

(10) Patent No.: US 8,263,615 B2
(45) Date of Patent: *Sep. 11, 2012

(54) BIS-HETEROCYCLIC IMIDAZOLYL COMPOUNDS

(75) Inventors: Peter Herold, Allschwil (CH); Robert Mah, Allschwil (CH); Vincenzo Tschinke, Allschwil (CH); Michael Quirmbach, Basel (CH); Christiane Marti, Allschwil (CH); Aleksandar Stojanovic, Allschwil (CH); Stefan Stutz, Allschwil (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/900,779

(22) Filed: Oct. 8, 2010

(65) Prior Publication Data

US 2011/0028512 A1    Feb. 3, 2011

Related U.S. Application Data

(62) Division of application No. 12/086,193, filed as application No. PCT/EP2006/069462 on Dec. 8, 2006, now Pat. No. 8,008,334.

(30) Foreign Application Priority Data

Dec. 9, 2005 (EP) ................................. 05111907

(51) Int. Cl.
- *A61K 31/437* (2006.01)
- *C07D 487/04* (2006.01)
- *C07D 471/04* (2006.01)
- *A61K 31/4188* (2006.01)
- *A61P 9/12* (2006.01)
- *A61P 3/06* (2006.01)
- *A61P 3/00* (2006.01)
- *A61P 9/04* (2006.01)

(52) U.S. Cl. ......... 514/300; 514/393; 546/121; 548/302

(58) Field of Classification Search .................. 514/300, 514/393; 548/302; 546/121

See application file for complete search history.

(56) References Cited

U.S. PATENT DOCUMENTS

| | | | |
|---|---|---|---|
| 4,889,861 A | 12/1989 | Browne | |
| 5,026,712 A | 6/1991 | Davey | |
| 5,057,521 A | 10/1991 | Häusler et al. | |
| 7,612,088 B2 * | 11/2009 | Herold et al. | 514/300 |
| 7,795,253 B2 | 9/2010 | Herold et al. | |
| 7,799,780 B2 | 9/2010 | Herold et al. | |
| 2004/0033935 A1 | 2/2004 | Tasaka et al. | |
| 2005/0043544 A1 | 2/2005 | Nuwa et al. | |
| 2006/0177506 A1 | 8/2006 | Yanai et al. | |
| 2007/0208035 A1 | 9/2007 | Herold et al. | |
| 2007/0225232 A1 * | 9/2007 | Herold et al. | 514/14 |
| 2008/0076784 A1 | 3/2008 | Herold et al. | |
| 2008/0076794 A1 | 3/2008 | Herold et al. | |
| 2008/0318978 A2 | 12/2008 | Herold et al. | |
| 2009/0012068 A1 | 1/2009 | Herold et al. | |
| 2009/0048241 A1 | 2/2009 | Herold et al. | |
| 2009/0053308 A1 | 2/2009 | Ishida et al. | |
| 2009/0111840 A1 | 4/2009 | Herold et al. | |
| 2009/0192144 A1 | 7/2009 | Herold et al. | |
| 2009/0192145 A1 | 7/2009 | Herold et al. | |
| 2009/0192149 A1 | 7/2009 | Herold et al. | |
| 2010/0010015 A1 | 1/2010 | Herold et al. | |
| 2010/0029694 A1 | 2/2010 | Herold et al. | |
| 2010/0168145 A1 | 7/2010 | Herold et al. | |
| 2010/0305110 A1 | 12/2010 | Herold et al. | |
| 2011/0028512 A1 | 2/2011 | Herold et al. | |
| 2011/0092492 A1 | 4/2011 | Herold et al. | |

FOREIGN PATENT DOCUMENTS

| | | | |
|---|---|---|---|
| EP | 1 471 056 | | 10/2004 |
| EP | 1 607 092 | | 12/2005 |
| JP | 63-145286 | | 6/1988 |
| WO | 97/00257 | | 1/1997 |
| WO | 02/40484 | | 5/2002 |
| WO | 2002040484 | * | 5/2002 |
| WO | 2004/082679 | | 9/2004 |
| WO | 2005118540 | * | 5/2005 |
| WO | 2005118557 | * | 5/2005 |
| WO | 2005118581 | * | 5/2005 |

OTHER PUBLICATIONS

International Search Report issued Jun. 1, 2007 in the International (PCT) Application PCT/EP2006/069462 of which the present application is the U.S. National Stage.
PCT Written Opinion in the International (PCT) Application PCT/EP2006/069462 of which the present application is the U.S. National Stage. Randall Lis et al., "Synthesis and Antiarrhythmic Activity of Novel 3-Alkyl-1-[ω[4-[(alkylsulfonyl)amino]phenyl]-ω-hydroxyalkyl]-1H-imidazolium Salts and Related Compounds", Journal of Medicinal Chemistry, American Chemical Society, vol. 30, No. 12, pp. 2303-2309, XP000575891, ISSN: 0022-2623, Dec. 1, 1987.
Translation of WO 97/00257 published Jan. 3, 1997.
Stewart et al., "Cortisol Response to Dextroamphetamine Stimulation in Depressed Outpatients", Psychiatry research, 1984, vol. 12, No. 3, pp. 195-206.

* cited by examiner

*Primary Examiner* — Niloofar Rahmani
(74) *Attorney, Agent, or Firm* — Wenderoth Lind & Ponack, L.L.P.

(57) ABSTRACT

Heterocyclic compounds of the general formula (I) are provided in which R, $R^1$, $R^2$, $R^3$, $R^4$ and n have the definitions elucidated in more detail in the description, to a process for preparing them and to the use of these compounds as medicaments, particularly as aldostereone synthase inhibitors,

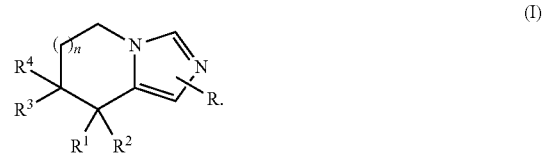

(I)

12 Claims, No Drawings

BIS-HETEROCYCLIC IMIDAZOLYL COMPOUNDS

This application is a Divisional of U.S. application Ser. No. 12/086,193, filed Jun. 6, 2008 now U.S. Pat. No. 8,008,334, which is a 371 application of PCT/EP2006/069462, filed Dec. 8, 2006.

The invention relates to new heterocyclic compounds, to processes for preparing the compounds, to pharmaceutical products comprising them, and to their use as active pharmaceutical ingredients, particularly as aldosterone synthase inhibitors.

The present invention first provides compounds of the general formula

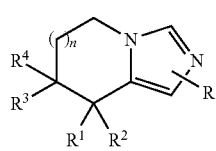

(I)

in which
R a) is deuterium, halogen, tri-$C_1$-$C_4$-alkylsilyl, trifluoromethoxy, trifluoromethyl or hydrogen; or
  b) is $C_1$-$C_8$-alkoxy or $C_1$-$C_8$-alkyl;
$R^1$ is aryl-$C_0$-$C_4$-alkyl or unsaturated heterocyclyl-$C_0$-$C_4$-alkyl, which radicals are substituted by 1-4 $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulphanyl, $C_1$-$C_8$-alkylsulphonyl, unsubstituted or substituted aryl, aryl-$C_0$-$C_4$-alkoxycarbonyl, cyano, halogen, unsubstituted or substituted heterocyclyl, hydroxyl, nitro, oxide, oxo, tri-$C_1$-$C_4$-alkylsilyl, trifluoromethoxy or trifluoromethyl;
$R^2$ a) is deuterium, halogen, hydroxyl or hydrogen; or
  b) is $C_2$-$C_8$-alkenyl, $C_2$-$C_8$-alkynyl, $C_1$-$C_8$-alkoxy, $C_1$-$C_4$-alkoxycarbonyl-$C_1$-$C_4$-alkyl, $C_1$-$C_8$-alkyl, $C_0$-$C_4$-alkylcarbonyl, aryl-$C_0$-$C_4$-alkyl, carboxy-$C_1$-$C_4$-alkyl, $C_3$-$C_8$-cycloalkyl or unsaturated heterocyclyl-$C_0$-$C_4$-alkyl, which radicals are unsubstituted or substituted by 1-4 $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulphonyl, unsubstituted or substituted aryl, aryl-$C_0$-$C_4$alkoxycarbonyl, cyano, halogen, unsubstituted or substituted heterocyclyl, hydroxyl, nitro, oxide, oxo, tri-$C_1$-$C_4$-alkylsilyl, trifluoromethoxy or trifluoromethyl;
$R^3$ a) is deuterium, halogen, hydroxyl, trifluoromethoxy, trifluoromethyl or hydrogen; or
  b) is $C_1$-$C_8$-alkoxy or $C_1$-$C_8$-alkyl;
$R^4$ a) is deuterium, halogen, trifluoromethoxy, trifluoromethyl or hydrogen; or
  b) is $C_1$-$C_8$-alkoxy or $C_1$-$C_8$-alkyl;
n is a number 0, 1 or 2;
and salts thereof, preferably pharmaceutically useful salts thereof,
where,
if $R^2$ is hydrogen $R^1$ is not carbazolyl, fluorenyl or naphthyl;
if R is hydrogen and $R^2$ is hydroxyl $R^1$ is not $C_1$-$C_8$-alkoxy- or halobenzothiophen-2-yl, unalkylated or N-mono- or N,N-di-$C_{1-8}$-alkylated carbamoylnaphthyl, unsubstituted or substituted biphenyl or 4-bromophenyl.

The present invention further provides compounds of the general formula (I), in which
(A) $R^1$ is phenyl or pyridyl if R, $R^2$, $R^3$ and $R^4$ are hydrogen and n is 0, whereby phenyl or pyridyl is substituted by 1-4 $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulphonyl, unsubstituted or substituted aryl, aryl-$C_0$-$C_4$-alkoxycarbonyl, cyano, halogen, unsubstituted or substituted heterocyclyl, hydroxyl, tri-$C_1$-$C_4$-alkylsilyl, trifluoromethoxy or trifluoromethyl, at least one substituent being located in the "para" position (relative to the 6,7-dihydro-5H-pyrrolo[1,2-c]imidazol-7-yl ring system); or
(B) $R^1$ is phenyl or unsaturated heterocyclyl if R, $R^2$, $R^3$ and $R^4$ are hydrogen and n is 1, whereby phenyl or unsaturated heterocyclyl is substituted by 3-4 $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulphonyl, unsubstituted or substituted aryl, aryl-$C_0$-$C_4$alkoxycarbonyl, cyano, halogen, unsubstituted or substituted heterocyclyl, tri-$C_1$-$C_4$-alkylsilyl, trifluoromethoxy or trifluoromethyl; or
(C) $R^1$ is aryl or unsaturated heterocyclyl, which radicals are substituted by 1-4 $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulphanyl, $C_1$-$C_8$-alkylsulphonyl, unsubstituted or substituted aryl, aryl-$C_0$-$C_4$-alkoxycarbonyl, cyano, halogen, unsubstituted or substituted heterocyclyl, hydroxyl, nitro, oxide, oxo, tri-$C_1$-$C_4$-alkylsilyl, trifluoromethoxy or trifluoromethyl, at least one substituent being $C_1$-$C_8$-alkylsulphanyl, hydroxyl, nitro or oxide; or
(D) $R^1$ is aryl or unsaturated heterocyclyl if $R^3$ and $R^4$ are both not simultaneously deuterium or hydrogen, whereby aryl or unsaturated heterocyclyl is substituted by 1-4 $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulphonyl, unsubstituted or substituted aryl, aryl-$C_0$-$C_4$-alkoxycarbonyl, cyano, halogen, unsubstituted or substituted heterocyclyl, oxo, tri-$C_1$-$C_4$-alkylsilyl, trifluoromethoxy or trifluoromethyl; or
(E) $R^1$ is aryl or unsaturated heterocyclyl if $R^2$ is hydroxyl or $C_1$-$C_8$-alkoxy, whereby aryl or unsaturated heterocyclyl is substituted by 1-4 $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulphonyl, unsubstituted or substituted aryl, aryl-$C_0$-$C_4$-alkoxycarbonyl, cyano, halogen, unsubstituted or substituted heterocyclyl, oxo, tri-$C_1$-$C_4$-alkylsilyl, trifluoromethoxy or trifluoromethyl;
R a) is deuterium, halogen, tri-$C_1$-$C_4$-alkylsilyl, trifluoromethoxy, trifluoromethyl or hydrogen; or
  b) is $C_1$-$C_8$-alkoxy or $C_1$-$C_8$-alkyl;
$R^2$ a) is deuterium, halogen, hydroxyl or hydrogen; or
  b) is $C_2$-$C_8$-alkenyl, $C_2$-$C_8$-alkynyl, $C_1$-$C_8$-alkoxy, $C_1$-$C_4$-alkoxycarbonyl-$C_1$-$C_4$-alkyl, $C_1$-$C_8$-alkyl, $C_0$-$C_4$-alkylcarbonyl, aryl-$C_0$-$C_4$-alkyl, carboxy-$C_1$-$C_4$-alkyl, $C_3$-$C_8$-cycloalkyl or unsaturated heterocyclyl-$C_0$-$C_4$-alkyl, which radicals may be substituted by 1-4 $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulphonyl, unsubstituted or substituted aryl, aryl-$C_0$-$C_4$-alkoxycarbonyl, cyano, halogen, unsubstituted or substituted heterocyclyl, hydroxyl, nitro, oxide, oxo, tri-$C_1$-$C_4$-alkylsilyl, trifluoromethoxy or trifluoromethyl;
$R^3$ a) is deuterium, halogen, hydroxyl, trifluoromethoxy, trifluoromethyl or hydrogen; or
  b) is $C_1$-$C_8$-alkoxy or $C_1$-$C_8$-alkyl;
$R^4$ a) is deuterium, halogen, trifluoromethoxy, trifluoromethyl or hydrogen; or
  b) is $C_1$-$C_8$-alkoxy or $C_1$-$C_8$-alkyl;
n is a number 0, 1 or 2;
and salts thereof, preferably pharmaceutically useful salts thereof,
where,
if $R^2$ is hydrogen $R^1$ is not carbazolyl, fluorenyl or naphthyl;

if R is hydrogen and $R^2$ is hydroxyl $R^1$ is not $C_1$-$C_8$-alkoxy- or halobenzothiophen-2-yl, unsubstituted or substituted biphenyl or 4-bromophenyl.

The term aryl stands for an aromatic hydrocarbon which contains generally 5-14, preferably 6-10, carbon atoms and is for example phenyl, or naphthyl, e.g. 1- or 2-naphthyl. Preference is given to aryl having 6-10 carbon atoms, particularly phenyl. Preferred is aryl which conforms to the Hückel rule. The stated radicals may be unsubstituted or substituted one or more times, such as once or twice, in which case the substituent may be in any position, such as in the o, m or p position of the phenyl radical or in the 3 or 4 position of the 1- or 2-naphthyl radical, and there may also be two or more identical or different substituents. Examples of substituents on aryl radicals or on the preferred phenyl or naphthyl radicals are as follows: $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulphonyl, unsubstituted or substituted aryl, aryl-$c_0$-$c_4$-alkoxycarbonyl, cyano, halogen, unsubstituted or substituted heterocyclyl, hydroxyl, nitro, tri-$C_1$-$C_4$-alkylsilyl, trifluoromethoxy or trifluoromethyl.

Aryl-$C_0$-$C_4$-alkyl is for example phenyl, naphthyl or benzyl.

The heterocyclyl term stands for a saturated, partially saturated or unsaturated, 4-8-membered, more preferably 5-membered, monocyclic ring system, for a saturated, partially saturated or unsaturated, 7-12-membered, more preferably 9-10-membered, bicyclic ring system and also for a partially saturated or unsaturated, 7-12-membered tricyclic ring system which contains an N, O or S atom in at least one of the rings, it being possible for an additional N, O or S atom to be present in one ring. The stated radicals may be unsubstituted or may be substituted one or more times, such as once or twice, and there may also be two or more identical or different substituents. Examples of substituents on heterocyclyl radicals are as follows: $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulphonyl, unsubstituted or substituted aryl, aryl-$C_0$-$C_4$-alkoxycarbonyl, cyano, halogen, unsubstituted or substituted heterocyclyl, hydroxyl, nitro, oxide, oxo, tri-$C_1$-$C_4$-alkylsilyl, trifluoromethoxy or trifluoromethyl.

Saturated heterocyclyl-$C_0$-$C_4$-alkyl is for example azepanyl, azetidinyl, aziridinyl, 3,4-dihydroxylpyrrolidinyl, 2,6-dimethylmorpholinyl, 3,5-dimethylmorpholinyl, dioxanyl, [1,4]dioxepanyl, dioxolanyl, 4,4-dioxothiomorpholinyl, dithianyl, dithiolanyl, 2-hydroxylmethyl-pyrrolidinyl, 4-hydroxylpiperidinyl, 3-hydroxylpyrrolidinyl, 4-methylpiperazinyl, 1-methyl-piperidinyl, 1-methylpyrrolidinyl, morpholinyl, oxathianyl, oxepanyl, 2-oxoazepanyl, 2-oxoimidazolidinyl, 2-oxooxazolidinyl, 2-oxopiperidinyl, 4-oxopiperidinyl, 2-oxopyrrolidinyl, 2-oxotetrahydropyrimidinyl, 4-oxothiomorpholinyl, piperazinyl, piperidinyl, pyrrolidinyl, tetrahydrofuranyl, tetrahydropyranyl, tetrahydrothiophenyl, tetrahydrothiopyranyl, thiepanyl or thiomorpholinyl.

Partially saturated bicyclic heterocyclyl-$C_0$-$C_4$-alkyl is for example 3,4-dihydro-2H-benzo-[1,4]oxazinyl, 4,5,6,7-tetrahydrobenzofuranyl or 4,5,6,7-tetrahydrobenzothiazolyl.

Unsaturated bicyclic heterocyclyl-$C_0$-$C_4$-alkyl is for example benzofuranyl, benzoimidazolyl, benzo[d]isothiazolyl, benzo[d]isoxazolyl, benzothiophenyl, quinolinyl, imidazo[1,5-a]pyridinyl, indazolyl, indolyl or isoquinolinyl.

Unsaturated monocyclic heterocyclyl-$C_0$-$C_4$-alkyl is for example imidazolyl, oxazolyl, pyridyl, pyrrolyl, tetrazolyl, thiazolyl or thiophenyl.

$C_2$-$C_8$-Alkenyl is for example ethenyl, propenyl, isopropenyl, butenyl, isobutenyl, secondary-butenyl, tertiary-butenyl, or a pentenyl, hexenyl or heptenyl group.

$C_2$-$C_8$-Alkynyl is for example ethynyl, propynyl, butynyl, or a pentynyl, hexynyl or heptynyl group.

$C_1$-$C_8$-Alkoxy is for example $C_1$-$C_5$-alkoxy, such as methoxy, ethoxy, propyloxy, isopropyloxy, butyloxy, isobutyloxy, secondary-butyloxy, tertiary-butyloxy or pentyloxy, but can also be a hexyloxy or heptyloxy group.

$C_1$-$C_8$-Alkoxycarbonyl is preferably $C_1$-$C_4$-alkoxycarbonyl, such as methoxycarbonyl, ethoxy-carbonyl, propyloxycarbonyl, isopropyloxycarbonyl, butyloxycarbonyl, isobutyloxycarbonyl, secondary-butyloxycarbonyl or tertiary-butyloxycarbonyl.

$C_1$-$C_4$-Alkoxycarbonyl-$C_1$-$C_4$-alkyl is for example methoxycarbonyl- or ethoxycarbonyl-methyl, 2-methoxycarbonyl- or 2-ethoxycarbonyl-ethyl, 3-methoxycarbonyl- or 3-ethoxycarbonyl-propyl or 4-ethoxycarbonylbutyl.

$C_1$-$C_8$-Alkyl can be linear or branched and/or bridged and is for example methyl, ethyl, propyl, isopropyl, butyl, isobutyl, secondary-butyl, tertiary-butyl, or a pentyl, hexyl or heptyl group.

$C_0$-$C_8$-Alkylcarbonyl is for example formyl, acetyl, propionyl, propylcarbonyl, isopropyl-carbonyl, butylcarbonyl, isobutylcarbonyl, secondary-butylcarbonyl or tertiary-butylcarbonyl.

Carboxy-$C_1$-$C_4$-alkyl is for example carboxymethyl, 2-carboxyethyl, 2- or 3-carboxypropyl, 2-carboxy-2-methylpropyl, 2-carboxy-2-ethylbutyl or 4-carboxybutyl, especially carboxymethyl.

$C_3$-$C_8$-Cycloalkyl is preferably 3-, 5- or 6-membered cycloalkyl, such as cyclopropyl, cyclopentyl, cyclohexyl.

Halogen is for example fluorine, chlorine, bromine or iodine.

The groups of compounds specified below should not be considered as being closed; on the contrary, parts of these groups of compounds may be replaced by one another or by the definitions given above, or may be omitted, in a meaningful way, such as in order to replace general definitions by more specific definitions. The stated definitions apply within the bounds of the general chemical principles, such as of the customary valencies for atoms, for example.

A preferred group for compounds of the formula (I) are compounds in which (A) $R^1$ is phenyl or pyridyl if R, $R^2$, $R^3$ and $R^4$ are hydrogen and n is 0, whereby phenyl or pyridyl is substituted by 1-4 $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulphanyl, $C_1$-$C_8$-alkylsulphonyl, unsubstituted or substituted aryl, aryl-$C_0$-$C_4$-alkoxycarbonyl, cyano, halogen, unsubstituted or substituted heterocyclyl, hydroxyl, nitro, oxide, tri-$C_1$-$C_4$-alkylsilyl, trifluoromethoxy or trifluoromethyl, at least one substituent being located in the "para" position (relative to the 6,7-dihydro-5H-pyrrolo[1,2-c]imidazol-7-yl ring system).

A further, preferred group of compounds of the formula (I) are compounds in which (B) $R^1$ is phenyl or unsaturated heterocyclyl if R, $R^2$, $R^3$ and $R^4$ are hydrogen and n is 1, whereby phenyl or unsaturated heterocyclyl is substituted by 3-4 $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulphanyl, $C_1$-$C_8$-alkylsulphonyl, unsubstituted or substituted aryl, aryl-$C_0$-$C_4$-alkoxycarbonyl, cyano, halogen, unsubstituted or substituted heterocyclyl, hydroxyl, nitro, tri-$C_1$-$C_4$-alkylsilyl, trifluoromethoxy or trifluoromethyl.

A further, preferred group of compounds of the formula (I) are compounds in which (C) $R^1$ is aryl or unsaturated heterocyclyl, which radicals are substituted by 1-4 $C_1$-$C_8$-alkoxy, $C_1$-$C_8$alkoxycarbonyl, $C_1$-$C_8$-alkyl, $C_0$-$C_8$-alkylcarbonyl, $C_1$-$C_8$-alkylsulphanyl, $C_1$-$C_8$-alkylsulphonyl, unsubstituted or substituted aryl, aryl-$C_0$-$C_4$-alkoxycarbonyl, cyano, halogen, unsubstituted or substituted heterocyclyl, hydroxyl, nitro, oxide, oxo, tri-$C_1$-$C_4$-alkylsilyl, trifluoromethoxy or trifluoromethyl, at least one substituent being $C_1$-$C_8$-alkylsulphanyl, hydroxyl, nitro or oxide.

A further, preferred group of compounds of the formula (I) are compounds in which (D) $R^1$ is aryl or unsaturated heterocyclyl if $R^3$ and $R^4$ are both not simultaneously deuterium or hydrogen, whereby aryl or unsaturated heterocyclyl is substituted by 1-4 $C_1$-$C_8$-alkoxy, $C_1$-$C_8$alkoxycarbonyl, $C_1$-$C_8$-alkyl, $C_0$-$C_8$alkylcarbonyl, $C_1$-$C_8$-alkylsulphanyl, $C_1$-$C_8$alkylsulphonyl, unsubstituted or substituted aryl, aryl-$C_0$-$C_4$-alkoxycarbonyl, cyano, halogen, unsubstituted or substituted heterocyclyl, hydroxyl, nitro, oxide, oxo, tri-$C_1$-$C_4$-alkylsilyl, trifluoromethoxy or trifluoromethyl.

A further, preferred group of compounds of the formula (I) are compounds in which (E) $R^1$ is aryl or unsaturated heterocyclyl if $R^2$ is hydroxyl or $C_1$-$C_8$alkoxy, whereby aryl or unsaturated heterocyclyl is substituted by 1-4 $C_1$-$C_8$-alkoxy, $C_1$-$C_8$alkoxycarbonyl, $C_1$-$C_8$-alkyl, $C_0$-$C_8$-alkylcarbonyl, $C_1$-$C_8$-alkylsulphanyl, $C_1$-$C_8$-alkylsulphonyl, unsubstituted or substituted aryl, aryl-$C_0$-$C_4$-alkoxycarbonyl, cyano, halogen, unsubstituted or substituted heterocyclyl, hydroxyl, nitro, oxide, oxo, tri-$C_1$-$C_4$-alkylsilyl, trifluoromethoxy or trifluoromethyl.

A further, preferred group of compounds of the formula (I) are compounds in which $R^1$ is pyridyl, under the conditions as specified for (A); or is phenyl, under the conditions as specified for (A) or (B); or is aryl or unsaturated heterocyclyl, substituted as specified under (C), (D) or (E), heterocyclyl being selected with particular preference from benzofuranyl, benzoimidazolyl, benzo[d]isothiazolyl, benzo[d]isoxazolyl, benzothiophenyl, imidazolyl, indazolyl, indolyl, oxazolyl, pyridyl, pyrrolyl, thiazolyl or thiophenyl;

and their salts, preferably their pharmaceutically useful salts,

A further, preferred group of compounds of the formula (I) are compounds in which $R^1$ has the definition as specified for (A), (B), (C), (D) or (E), more preferably as specified for (A), (B) or (C);

R is $C_1$-$C_8$-alkyl, deuterium, tri-$C_1$-$C_4$-alkylsilyl or hydrogen;

$R^2$ a) is deuterium, halogen, hydroxyl or hydrogen; or
  b) is $C_1$-$C_8$-alkoxy or $C_1$-$C_8$-alkyl;

$R^3$ a) is deuterium, halogen, hydroxyl or hydrogen; or
  b) is $C_1$-$C_8$-alkoxy or $C_1$-$C_8$-alkyl;

$R^4$ a) is deuterium, halogen or hydrogen; or
  b) is $C_1$-$C_8$-alkoxy or $C_1$-$C_8$-alkyl;

n is 0 or 1;
and their salts, preferably their pharmaceutically useful salts.

Additionally preferred are compounds of the formula (I) in which R is preferably $C_1$-$C_8$-alkyl, deuterium, tri-$C_1$-$C_4$-alkylsilyl or hydrogen, particularly preferably deuterium or hydrogen; and their salts, preferably their pharmaceutically useful salts.

Additionally preferred are compounds of the formula (I) in which $R^2$ is preferably $C_1$-$C_8$-alkoxy, $C_1$-$C_8$-alkyl, aryl-$C_0$-$C_4$-alkyl, deuterium, hydroxyl or hydrogen, particularly preferably $C_1$-$C_8$alkyl, deuterium, hydroxyl or hydrogen; and their salts, preferably their pharmaceutically useful salts.

Additionally preferred are compounds of the formula (I) in which $R^3$ is preferably $C_1$-$C_8$-alkyl, deuterium, halogen or hydrogen; and their salts, preferably their pharmaceutically useful salts.

Additionally preferred are compounds of the formula (I) in which $R^4$ is preferably $C_1$-$C_8$-alkyl, deuterium, halogen or hydrogen; and their salts, preferably their pharmaceutically useful salts.

n is preferably a number 0 or 1.

Preferred substituents for aryl or unsaturated heterocyclyl are $C_1$-$C_8$-alkoxy, $C_1$-$C_8$-alkyl, $C_1$-$C_8$alkylcarbonyl, $C_1$-$C_8$alkylsulphonyl, cyano, halogen, nitro, oxide, unsubstituted or substituted aryl, in particular unsubstituted or substituted phenyl, or unsubstituted or substituted heterocyyl, in particular unsubstituted or substituted tetrazolyl, unsubstituted or substituted thiazolyl or unsubstituted or substituted thiophenyl. Especially preferred substituents for aryl or unsaturated heterocyclyl are acetyl, chlorine, cyano, fluorine, methan-esulphonyl, nitro or oxide.

Preferably $R^1$ is unsubstituted or substituted 4-acetylphenyl, unsubstituted or substituted 4-cyanophenyl, unsubstituted or substituted 4-fluorophenyl, unsubstituted or substituted 4-methanesulphonylphenyl or unsubstituted or substituted 4-nitrophenyl.

Likewise preferably $R^1$ is a mono-, di- or tri-substituted unsaturated heterocyclyl substituent, the substituents being preferably selected from the group consisting of $C_1$-$C_8$-alkyl, $C_1$-$C_8$-alkoxy, $C_1$-$C_8$-alkoxycarbonyl, $C_0$-$C_8$-alkylcarbonyl, $C_1$-$C_8$-alkylsulphonyl, unsubstituted or substituted aryl, aryl-$C_0$-$C_4$-alkoxycarbonyl, cyano, halogen, unsubstituted or substituted heterocyclyl, hydroxyl, nitro, oxide, oxo, tri-$C_1$-$C_4$-alkylsilyl, trifluoromethoxy and trifluoromethyl.

With particular preference $R^1$ is benzofuran-3-yl, 1H-benzoimidazol-1-yl, benzo[d]isothiazol-3-yl, benzo[d]isoxazol-3-yl, benzo[b]thiophen-3-yl, imidazol-1-yl, indolyl, oxazol-4-yl, pyridin-4-yl, thiazol-4-yl or thiophen-3-yl, which radicals are substituted, and the substituents are preferably selected from the group consisting of $C_1$-$C_8$-alkyl, $C_1$-$C_8$-alkoxy, $C_1$-$C_8$-alkoxycarbonyl, $C_0$-$C_8$-alkylcarbonyl, $C_1$-$C_8$-alkylsulphonyl, unsubstituted or substituted aryl, aryl-$C_0$-$C_4$-alkoxycarbonyl, halogen, cyano, unsubstituted or substituted heterocyclyl, hydroxyl, nitro, oxide, oxo, tri-$C_1$-$C_4$-alkylsilyl, trifluoromethoxy and trifluoromethyl.

Also with very particular preference $R^1$ is 1H-benzoimidazol-1-yl, benzo[d]isothiazol-3-yl, benzo[d]isoxazol-3-yl, imidazol-1-yl or pyridin-4-yl, which radicals are substituted, and the substituents are preferably selected from the group consisting of $C_1$-$C_8$-alkyl, $C_1$-$C_8$-alkoxy, $C_1$-$C_8$-alkoxycarbonyl, $C_0$-$C_8$-alkylcarbonyl, $C_1$-$C_8$-alkylsulphonyl, unsubstituted or substituted aryl, aryl-$C_0$-$C_4$-alkoxycarbonyl, halogen, cyano, unsubstituted or substituted heterocyclyl, hydroxyl, nitro, oxide, oxo, tri-$C_1$-$C_4$-alkylsilyl, trifluoromethoxy and trifluoromethyl.

Additionally with particular preference $R^1$ is a mono-, di- or tri-substituted phenyl radical which has at least one substituent, preferably cyano, fluoro, acetyl, methanesulphonyl, nitro or unsubstituted or substituted heterocyclyl, the heterocycle preferably containing at least one nitrogen atom, in position 4.

Particular preference is given to compounds in which $R^2$ is hydrogen, deuterium, halogen, hydroxyl or $C_1$-$C_8$-alkyl and $R^4$ is hydrogen, deuterium or $C_1$-$C_8$-alkyl and in which $R^1$ is a mono-, di- or trisubstituted phenyl radical which has at least one substituent, preferably acetyl, methanesulphonyl, nitro or unsubstituted or substituted heterocyclyl, the heterocycle preferably containing at least one nitrogen atom, in position 4.

Likewise particularly preferred are compounds in which $R^2$ is deuterium, halogen, hydroxyl or $C_1$-$C_8$-alkyl and/or $R^4$ is deuterium or $C_1$-$C_8$-alkyl and in which $R^1$ is an unsubstituted or mono- or di-substituted 4-cyanophenyl radical or 4-fluorophenyl radical.

Likewise particularly preferred are compounds in which $R^1$ is a 4-cyano-3-trifluoromethyl-phenyl, 4-cyano-3-methoxyphenyl, 4-cyano-3-trifluoromethoxyphenyl, 3-bromo-4-cyanophenyl or 3-chloro-4-cyanophenyl, 3,5-difluoro-4-cyanophenyl, which if desired may be substituted by a further substituent on the phenyl radical, and $R^2$ and $R^4$ are hydrogen.

Likewise particularly preferred are compounds in which $R^1$ is an unsubstituted or mono- or di-substituted 4-cyanophenyl radical which is substituted in position 3 by an unsubstituted or mono-, di- or trisubstituted phenyl radical, and in which $R^2$ is hydrogen, deuterium, halogen, hydroxyl or $C_1$-$C_8$-alkoyl and $R^4$ is hydrogen, deuterium or $C_1$-$C_8$-alkyl.

Particularly preferred compounds of the formula (I) are those of the general formula (Ia)

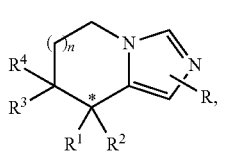

(Ia)

in which R, $R^1$, $R^2$, $R^3$, $R^4$ and n have the definitions specified above for the compounds of the formula (I), the above preferences applying analogously.

* denotes an asymmetric carbon atom.

The compounds of the formula (I) which possess at least one asymmetric carbon atom can exist in the form of optically pure enantiomers, mixtures of enantiomers, or racemates. Compounds having a second asymmetric carbon atom can exist in the form of optically pure diastereomers, mixtures of diastereomers, diastereomeric racemates, mixtures of diastereomeric racemates, or meso compounds. The invention embraces all of these forms. Mixtures of enantiomers, racemates, mixtures of diastereomers, diastereomeric racemates, or mixtures of diastereomeric racemates can be fractionated by conventional methods, such as by racemate resolution, column chromatography, thin-layer chromatography, HPLC and the like.

The compounds of the formula (Ia) have at least one asymmetric carbon atom, which is labelled "*". The compounds mentioned are to be understood as a single compound having a specific configuration around the designated asymmetric carbon atom. If a synthesis method is used which leads to racemic compounds, the racemate resolution is carried out in accordance with conventional methods, such as via a chiral HPLC column. Details are described in the examples. Compounds of the formula (Ia) as described in the present invention exhibit a pronounced aldosterone synthase and/or 11-β-hydroxylase inhibitory activity. The aforementioned activity can, readily and as described below, be determined via cellular assays based on the NCI-H295 R human adrenocortical carcinoma cell line. In the above-mentioned assay system, compounds of the formula (Ia) have an activity which is at least 20 times better, but preferably 40 times better, than the substances of the formula (Ia) with the opposite configuration around the asymmetric carbon atom labelled *.

The expression "pharmaceutically useful salts" embraces salts with organic or inorganic acids, such as hydrochloric acid, hydrobromic acid, nitric acid, sulphuric acid, phosphoric acid, citric acid, formic acid, maleic acid, acetic acid, succinic acid, tartaric acid, methane-sulphonic acid, p-toluenesulphonic acid and the like. Salts of compounds containing salt-forming groups are, in particular, acid addition salts, salts with bases or else, if appropriate, if two or more salt-forming groups are present, are mixed salts or inner salts.

The compounds of the formula (I) can be prepared analogously to preparation processes known from the literature (scheme).

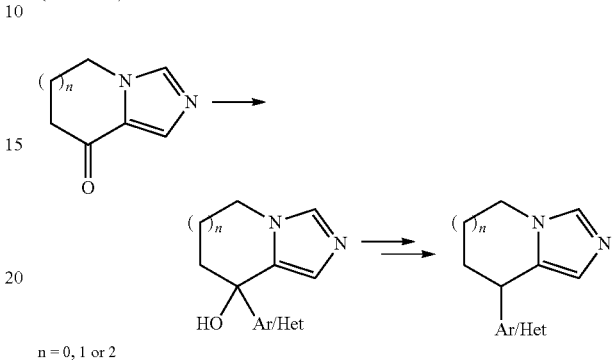

n = 0, 1 or 2
Ar = aryl; Het = unsaturated heterocyclyl

Details of the specific preparation variants can be found from the examples.

The compounds of the formula (I) can also be prepared in optically pure form. Separation into antipodes is possible by methods known per se, either, preferably, at an early stage in synthesis, by salt formation with an optically active acid such as, for example, (+)- or (−)-mandelic acid and separation of the diastereomeric salts by fractional crystallization, or, preferably, at a fairly late stage, by derivatization with a chiral auxiliary component, such as, for example, (+)- or (−)-camphanyl chloride and separation of the diastereomeric products by chromatography and/or crystallization and subsequent cleavage of the bond to the chiral auxiliary. The pure diastereomeric salts and derivatives can be analysed to determine the absolute configuration of the compound present, using customary spectroscopic methods, with single-crystal X-ray spectroscopy representing one particularly appropriate method.

Salts are primarily the pharmaceutically useful or non-toxic salts of compounds of the formula (I). Such salts are formed for example by compounds of the formula (I) containing an acidic group, such as a carboxyl or sulpho group and are, for example, salts thereof with suitable bases, such as non-toxic metal salts derived from metals of group Ia, Ib, IIa and IIb of the Periodic Table of the Elements, such as alkali metal salts, especially lithium, sodium or potassium salts, alkaline earth metal salts, magnesium or calcium salts for example, and also zinc salts or ammonium salts, and additionally salts formed with organic amines, such as unsubstituted or hydroxyl-substituted mono-, di- or trialkylamines, especially mono-, di- or tri-lower alkylamines, or with quaternary ammonium bases, e.g. methyl-, ethyl-, diethyl- or triethylamine, mono-, bis- or tris(2-hydroxyl-lower alkyl) amines, such as ethanolamine, diethanolamine or triethanolamine, tris(hydroxylmethyl)methylamine or 2-hydroxyl-tertiary-butylamine, N,N-di-lower alkyl-N-(hydroxyl-lower alkyl)amine, such as N,N-di-N-dimethyl-N-(2-hydroxylethyl)amine, or N-methyl-D-glucamine, or quaternary ammonium hydroxides, such as tetrabutylammonium hydroxide. The compounds of the formula (I) containing a basic group, such as an amino group, can form acid addition salts, with suitable inorganic acids for example, such as hydrohalic acid, such as hydrochloric acid, hydrobromic acid, or sulphuric acid with replacement of one or both protons, phosphoric acid with replacement of one or more protons, orthophosphoric acid or metaphosphoric acid for example, or pyrophosphoric acid with replacement of one or more protons, or with organic carboxylic, sulphonic or phosphonic acids or N-substituted sulphamic acids, e.g. acetic acid, propionic acid, glycolic acid, succinic acid, maleic acid, hydroxylmaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, and also amino acids, such as the α-amino acids specified earlier on, and also methanesulphonic acid, ethanesulphonic acid, 2-hydroxylethanesulphonic acid, ethane-1,2-disulphonic acid, benzenesulphonic acid, 4-toluenesulphonic acid, naphthalene-2-sulphonic acid, 2- or 3-phosphoglycerate, glucose 6-phosphate, N-cyclohexylsulphamic acid (to form cyclamates), or with other acidic organic compounds, such as ascorbic acid. Compounds of the formula (I) containing acidic and basic groups can also form inner salts.

Isolation and purification can also be carried out using pharmaceutically unsuitable salts.

The compounds of the formula (I) also include those compounds in which one or more atoms have been replaced by their stable, non-radioactive isotopes: for example, a hydrogen atom by deuterium.

Prodrug derivatives of the presently described compounds are derivatives thereof which when employed in vivo release the original compound as a result of a chemical or physiological process. A prodrug may be converted into the original compound, for example, when a physiological pH is reached or as a result of enzymatic conversion. Examples of possible prodrug derivatives include esters of freely available carboxylic acids, S- and O-acyl derivatives of thiols, alcohols or phenols, the acyl group being defined as above. Preference is given to pharmaceutically useful ester derivatives which are converted by solvolysis in physiological medium into the original carboxylic acid, such as, for example, lower alkyl esters, cycloalkyl esters, lower alkenyl esters, benzyl esters, mono- or disubstituted lower alkyl esters, such as lower ω-(amino, mono- or dialkylamino, carboxyl, lower alkoxycarbonyl)-alkyl esters or such as lower α-(alkanoyloxy, alkoxycarbonyl or dialkylaminocarbonyl)alkyl esters; pivaloyloxymethyl esters and similar esters are conventionally used as ester derivatives of this kind.

Because of the close relationship between a free compound, a prodrug derivative and a salt compound, a defined compound in this invention also includes its prodrug derivative and salt form, insofar as this is possible and appropriate.

Aldosterone is a steroidal hormone which is synthesized in the zona glomerulosa cells of the adrenal cortex by the enzyme aldosterone synthase (CYP11B2). Aldosterone production and secretion is regulated by the adrenocorticotropic hormone (ACTH), angiotensin II, potassium and sodium ions. The primary biological function of aldosterone is the regulation of the salt balance, with aldosterone controlling the reabsorption of sodium ions from the renal filtrate and the secretion of potassium ions into the renal filtrate. The state of excessive aldosterone secretion, also called hyperaldosteronism, can lead to high blood pressure, hypokalaemia, alkalosis, muscle weakness, polyuria, polydipsia, edemas, vasculitis, increased collagen formation, fibrosis and endothelial dysfunction.

The chemical compounds described in this invention inhibit the cytochrome P450 enzyme aldosterone synthase (CYP11B2) and can therefore be used to treat states induced by aldosterone. The compounds described can be employed for preventing, delaying the progression of or treating states such as hypokalaemia, hypertension, congestive heart failure, acute and—in particular—chronic renal failure, cardiovascular restenosis, atherosclerosis, metabolic syndrome (syndrome X), adiposity (obesity), vasculitis, primary and secondary hyperaldosteronism, nephropathy, myocardial infarction, coronary heart disease, increased collagen formation, fibrosis, vascular and coronary tissue changes (remodelling) secondary to high blood pressure, endothelial dysfunction, and oedemas secondary to cirrhosis, nephrosis and congestive heart failure.

Cortisol is a steroidal hormone which is synthesized almost exclusively in the zona fasciculata cells of the adrenal cortex by the cytochrome P450 enzyme 11-β-hydroxylase (CYP11B1). Cortisol production is regulated by ACTH. The primary biological function of cortisol is to regulate the production and the provision of carbohydrates for the brain and other metabolically active tissues. Increased cortisol production and secretion is a normal physiological response to stress and leads to the essential mobilization of fats, proteins and carbohydrates to cover increased physical energy demand. Chronically excessive cortisol release describes the condition of Cushing's syndrome. Cushing's syndrome may come about on the one hand as a result of cortisol hypersynthesis, which may be generated by an adrenocortical tumour, or on the other hand as the consequence of excessive stimulation of the adrenal cortex by ACTH. The first form is referred to as primary hypercortisolism, the second form as secondary hypercortisolism. An excessive and persistent cortisol secretion may also accompany a stress response, which can lead to depression and the suppression of the immune system.

The chemical compounds described in this invention inhibit the enzyme 11-β-hydroxylase (CYP11B1) and may therefore, owing to the inhibition of cortisol synthesis, be employed for preventing, delaying the progression of or treating Cushing's syndrome and also the physical and mental consequences of excessive and persistent cortisol secretion in states of stress.

The inhibition of aldosterone synthase (CYP11B2), as well as 11-β-hydroxylase (Cyp11B1) and aromatase (Cyp19) by herein described compounds may be measured by the following in vitro assay.

The cell line NCI-H295R was originally derived from an adrenal carcinoma and was subsequently characterized in the literature for the inducible secretion of steroidal hormones and the presence of the key enzymes necessary for steroidogenesis. These include Cyp11A (cholesterol side-chain cleavage), Cyp11B1 (steroid 11β-hydroxylase), Cyp11B2 (aldosterone synthase), Cyp17 (steroid 17α-hydroxylase and 17,20 lyase), Cyp19 (aromatase), Cyp21 B2 (steroid 21-hydroxylase) and 3β-HSD (hydroxysteroid dehydrogenase). The cells have the physiological characteristics of zonally undifferentiated human fetal adrenal cells, with the ability to produce the steroid hormones of each of the three phenotypically distinct zones found in the adult adrenal cortex.

The NCI-295R cells (American Type Culture Collection, ATCC, Rockville, Md., USA) are cultured in Dulbecco's Modified Eagle'Ham F-12 medium (DME/F12) that is supplemented with Ultroser SF serum (Soprachem, Cergy-Saint-Christophe, France) as well as insulin, transferrin, selenit (I-T-S, Becton Dickinson Biosiences, Franklin Lakes, N.J., USA) and antibiotics in 75 $cm^2$ cell culture flasks at a temperature of 37° C. and a 95% air/5% $CO_2$ humidified atmosphere. The cells are subsequently transferred to a 24-well plate and seeded in the presence of DME/F12 medium that is supplemented with 0.1% bovine serum albumin instead of Ultroser SF serum. The experiment is initiated by incubating the cells for 72 hours in DME/F12 medium supplemented with 0.1% bovine serum albumin and test compounds in the presence of cell stimulatory agents. The test compound is added in a concentration range of 0.2 nanomolar to 20 micromolar. Angiotensin-II (e.g. at 10 or 100 nanomolar concentration), potassium ions (e.g. at 16 millimolar), forskolin (e.g. at 10 micromolar) or a combination of two agents may serve as cell-stimulatory agents. The cellular secretion of aldosterone, cortisol, corticosterone and estradiol/estrone into the cell culture medium can be quantitatively assessed with commercially available radioimmunoassays and specific anti-bodies (e.g. Diagnostics Products Corporation, Los Angeles, Calif., USA) according to the manufacturer's instructions.

The degree of secretion of a selective steroid is used as a measure of enzyme activity, respectively enzyme inhibition, in the presence or absence of a test compound. The dose-dependent enzyme inhibitory activity of a compound is reflected in an inhibition curve that is characterized by an $IC_{50}$ value. The $IC_{50}$ values for active test compounds are generated by simple linear regression analysis to establish inhibition curves without data weighting. The inhibition curve is generated by fitting a 4-parameter logistic function to the raw data of the samples using the least squares approach. The function is described as follows:

$$Y=(d-a)/((1+(x/c)^{-b})+a)$$

with:
a=minimum
b=slope
c=$IC_{50}$
d=maximum
x=inhibitor concentrations

The compounds of the present invention show in the herein described in vitro test systems inhibitory activities with $IC_{50}$ values for aldosterone synthesis inhibition ranging from $10^{-4}$ to $10^{-10}$ mol/l, and $IC_{50}$ values for cortisol synthesis inhibition ranging from $10^{-4}$ to $10^{-10}$ mol/l.

The aldosterone- and corticosterone-suppressing activity of herein described compounds may be assessed with the following in vivo protocol.

Adult male Wistar rats weighing between 250 and 350 grams are kept under the usual 12 hour light and 12 hour dark conditions at a temperature of 23° C.±2° C. On the first day of the experiment, the animals receive a subcutaneous injection of a depot ACTH product in a dose of 1.0 mg/kg weight (SYNACTEN-Depot, Novartis, Basel, CH) 16 hours prior to the administration of a test compound. Pilot studies showed that this ACTH dose significantly increased plasma aldosterone and corticosterone levels by 5- to 20-fold over a period of at least 18 hours. An alternative method to stimulate aldosterone secretion consists in subjecting rats to a low salt diet for 48 hours and applying the diuretic furosemide at 10 mg/kg by subcutaneous or intraperitoneal administration 16 hours, respectively 2 hours prior to the start of the experiment. On the second day of the experiment, the animals are divided into test groups of 5 animals and subjected to a first bleed 1 hour prior to the administration of test compound. Subsequently, and 16 hours after the injection of the ACTH product, the animals receive either vehicle or test compound dissolved in vehicle in a variable dose range from 0.02 to 20 mg/kg by oral gavage. The animals are bled two more times from the vena subclavia under isoflurane anesthesia 2 and 6 hours after dosing. The blood is collected in heparin-treated tubes. The plasma samples are obtained by centrifugation and stored at −20° C. An alternative method to bleed animals time-dependently consists in using animals that are chronically carotid catheterized which allows the periodical sampling of up to 0.2 ml of blood using an AccuSampler (DiLab Europe, Lund, Sweden). The blood sampling with the AccuSampler may occur 1 hour prior to the administration of a test compound and 2, 4, 6, 8, 12, 16 and 24 hours thereafter. The blood samples are anti-coagulated with heparin and centrifuged. The aldosterone and corticosterone concentrations of the plasma samples can be determined with a radioimmunoassay as described above for the in vitro test systems.

The selective suppression of plasma steroid levels as for instance aldosterone in comparison to corticosterone may serve as a measure for in vivo bioavailability and pharmacodynamic enzyme inhibitory activity of the herein described compounds. The evaluation of the data may occur relative to the application of vehicle or quantitatively by determination of the area under the curve (AUC).

Examples of suppression of aldosterone and corticosterone levels:

| Compound of Example | Dose (mg/kg p.o.) | Aldosterone levels (% change[+] at 2 h) | Corticosterone levels (% change[+] at 2 h) |
|---|---|---|---|
| 2 | 4 | −49 | −32 |
| 3 | 4 | −53 | −13 |
| 12 | 4 | −61 | 2 |
| 13 | 4 | −62 | 0 |
| 16 | 4 | −21 | −3 |

[+]The resulting changes in plasma aldosterone, respectively corticosterone, levels upon oral administration of a test compound are expressed as percent (%) change that is defined by the ratio of the [(plasma steroid level 2 hours after compound administration) − (plasma steroid level 1 hour prior to compound administration)] divided by (plasma steroid level 1 hour prior to compound administration).

In order to achieve the desired effects in a patient to be treated, the compounds of the present invention can be administered orally or enterally, such as, for example, intravenously, intraperitoneally, intramuscularly, rectally, subcutaneously or else by direct injection of the active substance locally into tissues or tumours. The term patient encompasses warm-blooded species and mammals such as, for example, human, primate, bovine, dog, cat, horse, sheep, mouse, rat and pig. The compounds can be administered as pharmaceutical product or be incorporated into an administration device which ensures sustained release of the compound. The amount of substance to be administered can vary over a wide range and represent every effective dose. Depending on the patient to be treated or the condition to be treated and mode of administration, the dose of the effective substance each day can be between about 0.005 and 50 milligrams per kilogram of body weight, but is preferably between about 0.05 and 5 milligrams per kilogram of body weight each day.

For oral administration, the compounds can be formulated in solid or liquid pharmaceutical forms such as, for example, as capsules, pills, tablets, coated tablets, granules, powders, solutions, suspensions or emulsions. The dose of a solid pharmaceutical form can be one usual hard gelatine capsule which may be filled with active ingredients and excipients such as lubricants and fillers, such as, for example, lactose, sucrose and maize starch. Another form of administration may be represented by tableting of the active substance of the present invention. The tableting can take place with conventional tableting excipients such as, for example, lactose, sucrose, maize starch, combined with binder from gum acacia, maize starch or gelatine, disintegrants such as potato starch or crosslinked polyvinylpyrrolidone (PVPP) and lubricants such as stearic acid or magnesium stearate.

Examples of excipients suitable for soft gelatine capsules are vegetable oils, waxes, fats, semisolid and liquid polyols etc.

Examples of excipients suitable for producing solutions and syrups are water, polyols, sucrose, invert sugar, glucose etc.

For rectal administration, the compounds can be formulated in solid or liquid pharmaceutical forms such as, for example, suppositories. Examples of excipients suitable for suppositories are natural or hardened oils, waxes, fats, semi-liquid or liquid polyols etc.

For parenteral administration, the compounds can be formulated as injectable dosage of the active ingredient in a liquid or suspension. The preparations usually comprise a physiologically tolerated sterile solvent which may comprise a water-in-oil emulsion, with or without surfactant, and other pharmaceutically acceptable excipients. Oils which can be used for such preparations are paraffins and triglycerides of vegetable, animal or synthetic origin, such as, for example, peanut oil, soya oil and mineral oil. Injectable solutions generally comprise liquid carriers such as, preferably, water, saline, dextrose or related sugar solutions, ethanol and glycols such as propylene glycol or polyethylene glycol.

The substances may be administered as transdermal patch system, as depot injection or implant if the formulation makes sustained delivery of the active ingredient possible. The active substance can be compressed as granules or to narrow cylinders and be administered subcutaneously or intramuscularly as depot injection or implant.

The pharmaceutical products may in addition also comprise preservatives, solubilizers, viscosity-increasing substances, stabilizers, wetting agents, emulsifiers, sweeteners, colorants, aromatizing agents, salts to change the osmotic pressure, buffers, coating agents or antioxidants. They may also comprise other therapeutically valuable substances too.

The compounds of the invention described herein permit the following methods of use:
- as therapeutic combination in the form of a product or of a kit which is composed of individual components consisting of a compound described herein, in free form or as pharmaceutically useful salt, and at least one pharmaceutical form whose active ingredient has a blood pressure-lowering, an inotropic, an antidiabetic, an obesity-reducing or a lipid-lowering effect, which can be used either simultaneously or sequentially. The product and the kit may comprise instructions for use.
- as method for combined use, such as, for example, in simultaneous or sequential succession, of a therapeutically effective amount of a compound described herein, in free or in pharmaceutically useful salt form, and of a second active ingredient with blood pressure-lowering, inotropic, antidiabetic, obesity-reducing or lipid-lowering effect.

The compounds described herein and their pharmaceutically useful salts can be used in combination with
(i) one or more blood pressure-lowering active ingredients, as such for example:
  renin inhibitors such as aliskiren;
  angiotensin II receptor blockers such as candesartan, irbesartan, olmesartan, losartan, valsartan, telmisartan etc.;
  ACE inhibitors such as quinapril, ramipril, trandolapril, lisinopril, captopril, enalapril etc.;
  calcium antagonists such as nifedipine, nicardipine, verapamil, isradipine, nimodipine, amlodipine, felodipine, nisoldipine, diltiazem, fendiline, flunarizine, perhexyline, gallopamil etc.;
  diuretics such as hydrochlorothiazide, chlorothiazide, acetazolamide, amiloride, bumetanide, benzthiazide, etacrynic acid, furosemide, indacrinone, metolazone, triamterene, chlorthalidone, etc.;
  aldosterone receptor blockers such as spironolactone, eplerenone;
  endothelin receptor blockers such as bosentan;
  phosphodiesterase inhibitors such as amrinone, sildenafil;
  direct vasodilators such as dihydralazine, minoxidil, pinacidil, diazoxide, nitroprusside, flosequinan etc.,
  α- and β-receptor blockers such as phentolamine, phenoxybenzamine, prazosin, doxazosin, terazosin, carvedilol, atenolol, metoprolol, nadolol, propranolol, timolol, carteolol etc.;
  neutral endopeptidase (NEP) inhibitors;
  sympatholytics such as methyldopa, clonidine, guanabenz, reserpine
(ii) one or more agents having inotropic activity, as such for example:
  cardiac glycosides such as digoxin;
  β-receptor stimulators such as dobutamine
  thyroid hormone such as thyroxine
(iii) one or more agents having antidiabetic activity, as such for example:
  insulins such as insulin aspart, insulin human, insulin lispro, insulin glargine and further fast-, medium- and long-acting insulin derivatives and combinations
  insulin sensitizers such as rosiglitazone, pioglitazone;
  sulphonylureas such as glimepiride, chlorpropamide, glipizide, glyburide etc.;
  biguanides such as metformin;
  glucosidase inhibitors such as acarbose, miglitol;
  meglitinides such as repaglinide, nateglinide;
(iv) one or more obesity-reducing ingredients, as such for example:
  lipase inhibitors such as orlistat;
  appetite suppressants such as sibutramine, phentermine;
(v) one or more lipid-lowering ingredients, such as, for example,
  HMG-CoA reductase inhibitors such as lovastatin, fluvastatin, pravastatin, atorvastatin, simvastatin, rosuvastatin etc.;
  fibrate derivatives such as fenofibrate, gemfibrozil etc.;
  bile acid-binding active ingredients such as colestipol, colestyramine, colesevelam
  cholesterol absorption inhibitors such as ezetimibe
  nicotinic acid such as niacin and other agents which are suitable for the treatment of high blood pressure, heart failure or vascular disorders associated with diabetes and renal disorders, such as acute or chronic renal failure, in humans and animals. Such combinations can be used separately or in products which comprise a plurality of components.

The compounds described herein and their pharmaceutically useful salts can additionally be used in combination with
(i) a diagnostic test system which permits quantitative determination of the plasma aldosterone level (PAC, plasma aldosterone concentration)
(ii) a diagnostic test system which permits quantitative determination of the plasma renin level (PRC, plasma renin concentration)
(iii) a diagnostic test system which permits quantitative determination of the plasma renin activity (PRA, plasma renin activity)

(iv) a diagnostic test system which permits quantitative determination of the plasma aldosterone/renin level (ARC, aldosterone renin concentration)
(v) a diagnostic test system which permits quantitative determination of the plasma aldosterone/renin activity (ARR, aldosterone to renin activity ratio)
(vi) a diagnostic test system which permits quantitative determination of the plasma cortisol level (PCC, plasma cortisol concentration)

Such diagnosis-therapy combinations can be used separately or in products which comprise a plurality of components.

The following examples illustrate the present invention. All temperatures are stated in degrees Celsius, pressures in mbar. Unless mentioned otherwise, the reactions take place at room temperature. The abbreviation "Rf=xx(A)" means for example that the Rf is found in solvent system A to have the value xx. The proportion of solvents to one another is always stated in fractions by volume. Chemical names of end products and intermediates were generated with the aid of the AutoNom 2000 (Automatic Nomenclature) program.

HPLC gradients on Hypersil BDS C-18 (5 µm); column: 4×125 mm
(I) 99% water*/1% acetonitrile* to 0% water*/100% acetonitrile* in 10 minutes+2 minutes (1 ml/min)
* contains 0.1% trifluoroacetic acid The abbreviations used are as follows:
Rf ratio of distance traveled by a substance to distance of the eluent from the starting point in thin-layer chromatography
Rt retention time of a substance in HPLC (in minutes)
m.p. melting point (temperature)

1
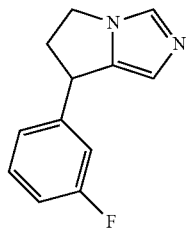

2
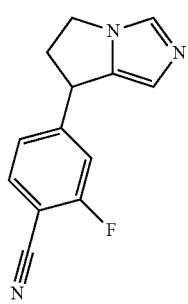

3
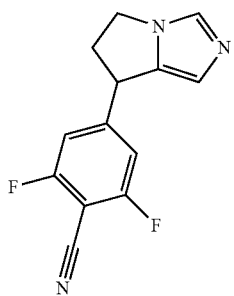

4
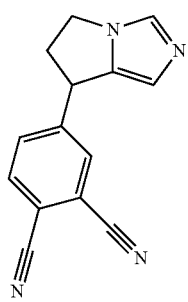

5
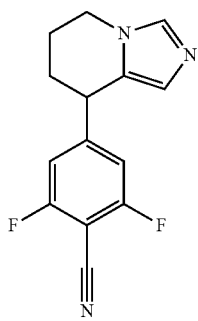

6
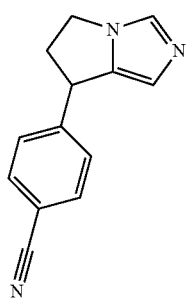

7
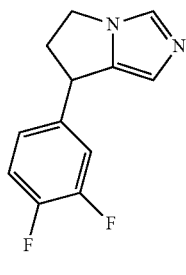

8
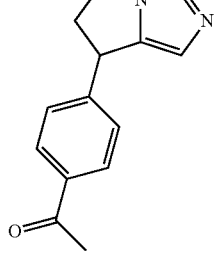

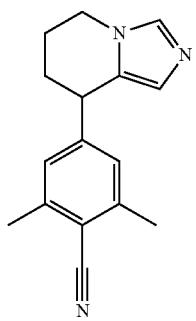
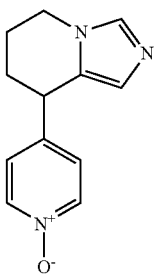
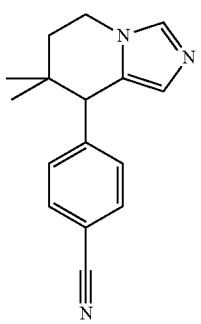
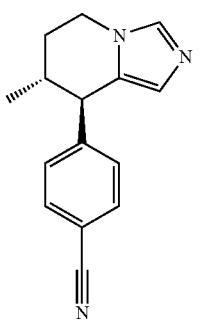
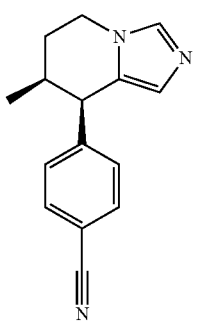
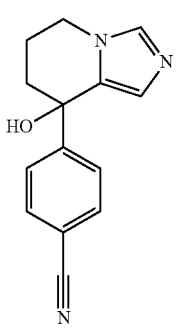

-continued

20

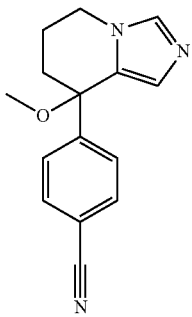

21

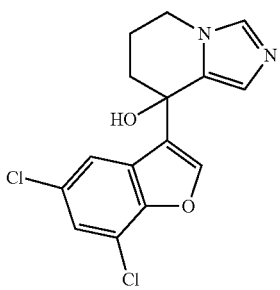

22

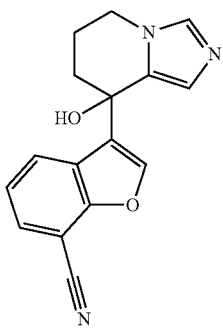

23

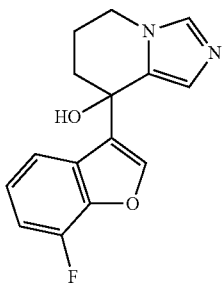

EXAMPLE 1

4-(6,7-Dihydro-5H-pyrrolo[1,2-c]imidazol-7-yl)benzonitrile

A solution of 0.99 mmol of 4-(5H-pyrrolo[1,2-c]imidazol-7-yl)benzonitrile in 15 ml of MeOH is hydrogenated in the presence of 123 mg of 10% Pd/C at room temperature for 5.5 hours. The reaction mixture is subjected to clarifying filtration and the filtrate is evaporated. From the residue the title compound is obtained by means of flash chromatography (SiO₂ 60 F) as a pale reddish solid. Rf=0.22 (dichloromethane/ammonia (2M in EtOH) 97:3), Rt=4.43 (Gradient I).

The starting materials are prepared as follows:

a) 4-(5H-Pyrrolo[1,2-c]imidazol-7-yl)-benzonitrile

A mixture of 2.35 mmol of 4-(7-hydroxyl-6,7-dihydro-5H-pyrrolo[1,2-c]imidazol-7-yl)-benzonitrile in 5 ml of tetrahydrofuran and 10 ml of 4N HCl is stirred at 50° C. for 12 hours. The reaction mixture is cooled to room temperature, poured onto ice/4N NaOH and extracted with ethyl acetate (3×). The combined organic phases are dried with sodium sulphate and evaporated. From the residue the title compound is obtained by means of flash chromatography (SiO₂ 60 F) as a light brown solid. Rt=4.55 (Gradient I).

Alternatively the title compound can also be prepared as follows:

A solution of 4 mmol of 4-(7-hydroxyl-6,7-dihydro-5H-pyrrolo[1,2-c]imidazol-7-yl)-benzonitrile and 8 mmol of thionyl chloride in 30 ml of chloroform is heated at reflux for 15 hours. The reaction mixture is cooled to room temperature and poured into saturated sodium hydrogen carbonate solution. The phases are separated and the organic phase is washed with brine, dried with sodium sulphate and evaporated. From the residue the title compound is obtained by means of flash chromatography (SiO₂ 60 F).

b) 4-(7-Hydroxyl-6,7-dihydro-5H-pyrrolo[1,2-c]imidazol-7-yl)-benzonitrile

A solution of 8.18 mmol of 4-iodobenzonitrile [3058-39-7] in 20 ml of tetrahydrofuran at −20° C. is admixed dropwise with 8.18 mmol of isopropylmagnesium chloride (2M in tetrahydrofuran) and the reaction mixture is subsequently stirred for 15 minutes. A mixture of 4.09 mmol of 5,6-dihydropyrrolo[1,2-c]imidazol-7-one [426219-43-4] in 5 ml of tetrahydrofuran is added. After 1 hour the reaction mixture is poured into 1:1 1N HCl/dichloromethane and the phases are separated. The aqueous phase is rendered basic with saturated sodium hydrogen carbonate solution, stirred thoroughly, extracted with tert-butyl methyl ether (in order to separate unreacted ketone) and then extracted with dichloromethane (3×). The combined dichloromethane phases are dried with sodium sulphate and evaporated. From the residue the title compound is obtained by means of flash chromatography (SiO₂ 60 F) as a white foam. Rf=0.20 (dichloromethane/ammonia (2M in EtOH) 95:5), Rt=3.81 (Gradient I).

By the process described in Example 1 the following compounds are prepared analogously:

2  7-(3,4-Difluorophenyl)-6,7-dihydro-5H-pyrrolo[1,2-c]imidazole starting from 1,2-difluoro-4-iodobenzene [64248-58-4]
4  7-(3-Fluorophenyl)-6,7-dihydro-5H-pyrrolo[1,2-c]imidazole starting from 1-fluoro-3-iodobenzene [1121-86-4]
5  4-(6,7-Dihydro-5H-pyrrolo[1,2-c]imidazol-7-yl)-2-fluorobenzonitrile starting from 2-fluoro-4-iodobenzonitrile [137553-42-5]
6  4-(6,7-Dihydro-5H-pyrrolo[1,2-c]imidazol-7-yl)-2,6-difluorobenzonitrile starting from 2,6-difluoro-4-iodobenzonitrile [141743-50-2]
7  4-(6,7-Dihydro-5H-pyrrolo[1,2-c]imidazol-7-yl)phthalonitrile starting from 4-iodophthalonitrile [69518-17-8]
8  2,6-Difluoro-4-(5,6,7,8-tetrahydroimidazo[1,5-a]pyridin-8-yl)benzonitrile starting from 6,7-dihydro-5H-imidazo[1,5-a]pyridin-8-one [426219-51-4] and 2,6-difluoro-4-iodobenzonitrile [141743-50-2]
9  2,6-Dimethyl-4-(5,6,7,8-tetrahydroimidazo[1,5-a]pyridin-8-yl)benzonitrile starting from 6,7-dihydro-5H-imidazo[1,5-a]pyridin-8-one [426219-51-4] and 4-iodo-2,6-dimethylbenzonitrile [160682-00-8]

10  8-(5,7-Dichloro-2-methylbenzofuran-3-yl)-5,6,7,8-tetrahydroimidazol-[1,5-a]pyridine starting from 6,7-dihydro-5H-imidazo[1,5-a]pyridin-8-one [426219-51-4] and 5,7-dichloro-3-iodo-2-methylbenzofuran.

The starting material is prepared as follows:

a) 5,7-Dichloro-3-iodo-2-methylbenzofuran

A suspension of 1.7 mmol of pulverized iodine in 10 ml of glacial acetic acid is admixed with 3 mmol of 5,7-dichloro-2-methylbenzofuran [42969-85-7] and with 0.3 mmol of sodium nitrate. The mixture is stirred at 85° C. for 6 hours. If necessary further sodium nitrate is added after 1 hour. The reaction mixture is cooled to room temperature and quenched with 10% sodium hydrogen sulphite solution, and tert-butyl methyl ether is added. The phases are separated and the aqueous phase is extracted with tert-butyl methyl ether (3×). The combined organic phases are washed with brine, dried with sodium sulphate and evaporated. From the residue the title compound is identified by means of flash chromatography ($SiO_2$ 60 F) on the basis of the Rf value.

11  8-(4-Nitrophenyl)-5,6,7,8-tetrahydroimidazo[1,5-a]pyridine starting from 6,7-dihydro-5H-imidazo[1,5-a]pyridin-8-one [426219-51-4] and 1-iodo-4-nitro-benzene [636-98-6]

19  4-(8-Hydroxyl-5,6,7,8-tetrahydroimidazo[1,5-a]pyridin-8-yl)benzonitrile starting from 6,7-dihydro-5H-imidazo[1,5-a]pyridin-8-one [426219-51-4] and 4-iodo-benzonitrile [3058-39-7]

EXAMPLE 3

1-[4-(6,7-Dihydro-5H-pyrrolo[1,2-c]imidazol-7-yl)phenyl]ethanone

In the same way as in Example 1 and 1a 8-[4-(1,1-dimethoxyethyl)phenyl]-5,6,7,8-tetrahydro-imidazo[1,5-a]pyridin-8-ol is reacted. The title compound is obtained as a brownish oil. Rf=0.28 (dichloromethane/methanol 95:5), Rt=4.73 (Gradient I).

The starting material is prepared as follows:

a) 8-[4-(1,1-Dimethoxyethyl)phenyl]-5,6,7,8-tetrahydroimidazo[1,5-a]pyridin-8-ol The Grignard reagent, prepared from 3.68 mmol of 1-bromo-4-(1,1-dimethoxyethyl)benzene [53578-00-0] and 14.72 mmol of magnesium in 5.5 ml of tetrahydrofuran is added slowly dropwise to a solution of 1.84 mmol of 6,7-dihydro-5H-imidazo[1,5-a]pyridin-8-one [426219-51-4] in 10 ml of tetrahydrofuran under argon. The reaction mixture is stirred at room temperature for 12 hours and then quenched with 0.5N HCl. It is extracted with dichloromethane and the phases are separated. The aqueous phase is rendered basic with sodium hydrogen carbonate and the precipitated solid is isolated by filtration and dried at 40° C. The title compound is obtained as a greyish solid. Rt=3.42 (Gradient I). By the process described in Example 3 the following compounds are prepared analogously:

21  8-(5,7-Dichlorobenzofuran-3-yl)-5,6,7,8-tetrahydroimidazo[1,5-a]pyridin-8-ol starting from 6,7-dihydro-5H-imidazo[1,5-a]pyridin-8-one [426219-51-4] and 3-bromo-5,7-dichlorobenzofuran [99660-98-7].

22  3-(8-Hydroxy-5,6,7,8-tetrahydroimidazo[1,5-a]pyridin-8-yl)benzofuran-7-carbonitrile starting from 6,7-dihydro-5H-imidazo[1,5-a]pyridin-8-one [426219-51-4] and 3-bromo-benzofuran-7-carbonitrile [215801-96-0].

23  8-(7-Fluorobenzofuran-3-yl)-5,6,7,8-tetrahydroimidazo[1,5-a]pyridin-8-ol starting from 6,7-dihydro-5H-imidazo[1,5-a]pyridin-8-one [426219-51-4] and 3-bromo-7-fluorobenzofuran [1288851-92-3].

EXAMPLE 12

8-(4-Methylsulphanylphenyl)-5,6,7,8-tetrahydroimidazo[1,5-a]pyridine 12.6 mmol of sodium borohydride are suspended in 6 ml of tetrahydrofuran. 19.1 mmol of boron trifluoride ethyl etherate are added dropwise at 0° C. and the reaction mixture is stirred thoroughly for 10 minutes. A suspension of 1.27 mmol of 8-(4-methylsulphanylphenyl)-5,6,7,8-tetrahydroimidazo[1,5-a]pyridin-8-ol in 6 ml of tetrahydrofuran is added and the reaction mixture is stirred at room temperature for 16 hours. The reaction mixture is subsequently poured into saturated aqueous sodium hydrogen carbonate solution and extracted with dichloromethane (3×). The combined organic phases are dried with sodium sulphate and evaporated. From the residue the title compound is obtained by means of flash chromatography ($SiO_2$ 60 F) as a white solid. Rf=0.63 (dichloromethane/methanol 9:1); Rt=5.73 (Gradient I).

The starting material is prepared as follows:

a) 8-(4-Methylsulphanylphenyl)-5,6,7,8-tetrahydroimidazo[1,5-a]pyridin-8-ol

In analogy to Example 3a 4-thioanisolemagnesium bromide is reacted. The title compound is obtained as a white solid. Rt=5.04 (Gradient I).

EXAMPLE 13

8-(2-Nitrophenyl)-5,6,7,8-tetrahydroimidazo[1,5-a]pyridine 0.055 ml of sulphuric acid is added slowly dropwise at 0° C. to 0.046 ml of nitric acid. The nitrating acid is subsequently added slowly dropwise at 0° C. to 0.69 mmol of 8-phenyl-5,6,7,8-tetrahydroimidazo[1,5-a]pyridine. The reaction mixture is subsequently stirred at 0° C. for 5 minutes and then poured into ice-water. The aqueous phase is rendered neutral with saturated aqueous sodium hydrogen carbonate solution and extracted with dichloromethane (3×). The combined organic phases are dried over magnesium sulphate and evaporated. From the residue the title compound is obtained by means of flash chromatography ($SiO_2$ 60 F) as a brown wax. Rf=0.25 (dichloromethane/ammonia (2M in EtOH) 97:3), Rt=5.10 (Gradient I).

The starting materials are prepared as follows:

a) 8-Phenyl-5,6,7,8-tetrahydroimidazo[1,5-a]pyridine

In analogy to Example 3 8-phenyl-5,6,7,8-tetrahydroimidazo[1,5-a]pyridin-8-ol is reacted. The title compound is obtained as a beige solid. Rf=0.40 (toluene/methanol 85:15); Rt=5.03 (Gradient I).

b) 8-Phenyl-5,6,7,8-tetrahydroimidazo[1,5-a]pyridin-8-ol

In analogy to Example 3a 6,7-dihydro-5H-imidazo[1,5-a]pyridin-8-one [426219-51-4] and phenylmagnesium bromide solution [100-58-3] (1M in tetrahydrofuran) are reacted. The title compound is obtained as a beige solid. Rt=4.10 (Gradient I).

EXAMPLE 14

8-(1-Oxypyridin-4-yl)-5,6,7,8-tetrahydroimidazo[1,5-a]pyridine

A solution of 0.53 mmol of 8-pyridin-4-yl-5,6,7,8-tetrahydroimidazo[1,5-a]pyridine in 5 ml of acetic acid at room temperature is admixed with 0.53 mmol of hydrogen peroxide (30% in water) and stirred at 80° C. for 24 hours. The reaction mixture is cooled to room temperature, admixed with sodium sulphite and then evaporated. The residue is stirred thoroughly while hot with acetone and the mixture is filtered and evaporated again. From the residue the title compound is identified by means of flash chromatography (SiO$_2$ 60 F) on the basis of the Rf value.

The starting material is prepared as follows:

a) 8-Pyridin-4-yl-5,6,7,8-tetrahydroimidazo[1,5-a]pyridine

In analogy to Example 1 6,7-dihydro-5H-imidazo[1,5-a]pyridin-8-one [426219-51-4] and 4-iodopyridine [15854-87-2] are reacted. The title compound is obtained as a light brown foam. Rt=2.26 (Gradient I).

EXAMPLE 16

4-(7,7-Dimethyl-5,6,7,8-tetrahydroimidazo[1,5-a]pyridin-8-yl)benzonitrile 1.03 mmol of trifluoromethanesulphonic acid 4-(7,7-dimethyl-5,6,7,8-tetrahydroimidazo-[1,5-a]pyridin-8-yl)phenyl ester and 2.06 mmol of zinc(II) cyanide are introduced under argon in 10 ml of absolute N,N-dimethylformamide. The reaction mixture is admixed with 0.05 mmol of [1,1'-bis(diphenylphosphino)ferrocene]dichloropalladium and stirred at 120° C. for 20 hours. The reaction mixture is poured into ice-water and extracted with tert-butyl methyl ether (3×). The combined organic phases are dried with magnesium sulphate and evaporated. From the residue the title compound is obtained by means of flash chromatography (SiO$_2$ 60 F) as a pale pink solid. Rf=0.17 (dichloromethane/ammonia (2M in EtOH) 97:3), Rt=5.40 (Gradient I).

The starting materials are prepared as follows:

a) Trifluoromethanesulphonic acid 4-(7,7-dimethyl-5,6,7,8-tetrahydroimidazo[1,5-a]pyridin-8-yl)phenyl ester 1.30 mmol of 4-(7,7-dimethyl-5,6,7,8-tetrahydroimidazo[1,5-a]pyridin-8-yl)phenol are taken up under argon in 10 ml of absolute N,N-dimethylformamide. The reaction mixture is cooled to 0-5° C. and admixed with 2.90 mmol of sodium hydride (60% dispersion in paraffin). The reaction mixture is subsequently stirred at 0° C. for 30 minutes and then a solution of 2.53 mmol of N-phenyltrifluoromethanesulphonimide in 5 ml of absolute N,N-dimethyl-formamide is added dropwise. The reaction mixture is subsequently stirred at room temperature for 2 hours, poured into water and extracted with tert-butyl methyl ether (3×). The combined organic phases are dried over magnesium sulphate and evaporated. From the residue the title compound is obtained by means of flash chromatography (SiO$_2$ 60 F) as a beige solid. Rf=0.22 (dichloromethane/ammonia (2 M in EtOH) 97:3), Rt=7.00 (Gradient I).

b) 4-(7,7-Dimethyl-5,6,7,8-tetrahydroimidazo[1,5-a]pyridin-8-yl)phenol

A solution of 3.30 mmol of 8-(4-methoxyphenyl)-7,7-dimethyl-5,6,7,8-tetrahydro-imidazo[1,5-a]pyridine in 50 ml of dichloromethane is admixed dropwise at 0-5° C. with 8.25 mmol of boron tribromide (1M solution in dichloromethane). The reaction solution is subsequently stirred at 0° C. for 1 hour, then admixed with saturated aqueous sodium hydrogen carbonate solution and extracted with dichloromethane (3×). The combined organic phases are dried over magnesium sulphate and evaporated. The residue is taken up in 0.5N NaOH and the mixture is extracted with ethyl acetate (3×). The combined organic phases are dried over magnesium sulphate and evaporated. The title compound is obtained as a beige solid and used without further purification for the next stage. Rt=4.91 (Gradient I).

c) 8-(4-Methoxyphenyl)-7,7-dimethyl-5,6,7,8-tetrahydroimidazo[1,5-a]pyridine

A solution of 3.50 mmol of 8-(4-methoxyphenyl)-7,7-dimethyl-5,6,7,8-tetrahydro-imidazo[1,5-a]pyridin-8-ol in 10 ml of ethanol is admixed with 3.5 mmol of concentrated sulphuric acid and 0.70 mmol of 10% Pd/C and the reaction mixture is hydrogenated in an autoclave at 4 bar and 60° C. for 4-8 hours. The reaction mixture is filtered over Hyflo and the filtrate is concentrated. The title compound is used without further purification for the next stage. Rt=5.89 (Gradient I).

d) 8-(4-Methoxyphenyl)-7,7-dimethyl-5,6,7,8-tetrahydroimidazo[1,5-a]pyridin-8-ol A solution of 7.90 mmol of 7,7-dimethyl-6,7-dihydro-5H-imidazo[1,5-a]pyridin-8-one in 50 ml of tetrahydrofuran is admixed at 0-5° C. with 15.8 mmol of 4-methoxyphenylmagnesium bromide (0.5M solution in tetrahydrofuran). The reaction solution is subsequently stirred at 0° C. for 1 hour and then at room temperature for 16 hours. The reaction solution is hydrolysed with 0.5N HCl and extracted with tert-butyl methyl ether. The aqueous phase is rendered basic with saturated aqueous sodium hydrogen carbonate solution and the precipitated solid is isolated by filtration and dried. The title compound is obtained as a grey solid and used without further purification for the next stage. Rt=5.42 (Gradient I).

e) 7,7-Dimethyl-6,7-dihydro-5H-imidazo[1,5-a]pyridin-8-one 21.4 mmol of potassium hydride (35% dispersion in oil) are washed with hexane (2×) and then taken up under argon in 10 ml of absolute tetrahydrofuran. A solution of 7.12 mmol of 6,7-dihydro-5H-imidazo[1,5-a]pyridin-8-one [426219-51-4] in 5 ml of tetrahydrofuran is added at 0° C. A solution of 15.7 mmol of methyl iodide in 5 ml of tetrahydrofuran is added dropwise over 1 hour and the reaction mixture is subsequently stirred at room temperature for 16 hours. It is quenched with water and the mixture is extracted with dichloromethane. The combined organic phases are washed with brine, dried over sodium sulphate and evaporated. From the reside the title compound is obtained by means of flash chromatography (SiO$_2$ 60 F) as a yellowish solid. Rt=3.42 (Gradient I).

By the process described in Example 16 the following compounds are prepared analogously:

17  4-((7,8 trans)-7-Methyl-5,6,7,8-tetrahydroimidazo[1,5-a]pyridin-8-yl)benzonitrile starting from 4-iodobenzonitrile [3058-39-7] and (R,S)-7-methyl-6,7-dihydro-5H-imidazo-[1,5-a]pyridin-8-one. The diastereomers are separated at the final stage. The title compound is identified on the basis of the Rf value.

The starting material is prepared as follows:

a) (R,S)-7-Methyl-6,7-dihydro-5H-imidazo[1,5-a]pyridin-8-one

A solution of 1.5 mmol of 6,7-dihydro-5H-imidazo[1,5-a]pyridin-8-one [426219-51-4] in 5 ml of tetrahydrofuran is cooled to 0° C. and admixed in portions with 1.5 mmol of potassium hydride (35% dispersion in oil). The mixture is subsequently stirred at 0° C. for 1 hour and 1.5 mmol of methyl iodide is added at 0° C. The reaction mixture is slowly warmed to room temperature. It is quenched with saturated ammonia chloride solution. The phases are separated and the aqueous phase is extracted with diethyl ether (3×). The combined organic phases are washed with brine, dried over sodium sulphate and evaporated. From the residue the title compound is identified by means of flash chromatography (SiO$_2$ 60 F) on the basis of the Rf value.

18  4-((7,8 cis)-7-Methyl-5,6,7,8-tetrahydroimidazo[1,5-a]pyridin-8-yl)benzonitrile starting from 4-iodobenzonitrile [3058-39-7] and (R,S)-7-methyl-6,7-dihydro-5H-imidazo-[1,5-a]pyridin-8-one (Example 17a). The diastereomers are separated at the final stage. The title compound is identified on the basis of the Rf value.

EXAMPLE 20

4-(8-Methoxy-5,6,7,8-tetrahydroimidazo[1,5-a]pyridin-8-yl)benzonitrile

A suspension of 0.63 mmol of 4-(8-hydroxyl-5,6,7,8-tetrahydroimidazo[1,5-a]pyridin-8-yl)-benzonitrile (Example 19) in 2 ml of tetrahydrofuran is added at 0° C. to a suspension of 0.76 mmol of sodium hydride (60% dispersion in paraffin) in 1 ml of tetrahydrofuran. The reaction mixture is subsequently stirred at 20° C. for 30 minutes and then cooled again to 0° C. A solution of 0.63 mmol of methyl iodide in 3 ml of N,N-dimethylformamide is added dropwise and the reaction mixture is subsequently stirred at room temperature for 16 hours. The reaction mixture is poured into water and extracted with tert-butyl methyl ether (3×). The combined organic phases are dried over sodium sulphate and evaporated. The residue is digested with diethyl ether and the solid is isolated by filtration and dried. The title compound is obtained as a white solid. Rf=0.14 (toluene/methanol 85:15), Rt=4.92 (Gradient I).

The invention claimed is:

1. Compound of the general formula

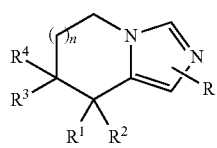

(I)

in which (B) $R^1$ is phenyl or unsaturated heterocyclyl if R, $R^2$, $R^3$ and $R^4$ are hydrogen and n is 1, whereby phenyl or unsaturated heterocyclyl is substituted by 3-4 $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulphonyl, unsubstituted or substituted aryl, aryl-$C_0$-$C_4$-alkoxycarbonyl, cyano, halogen, unsubstituted or substituted heterocyclyl, tri-$C_1$-$C_4$-alkylsilyl, trifluoromethoxy or trifluoromethyl; or (C) $R^1$ is aryl or unsaturated heterocyclyl, which radicals are substituted by 1-4 $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulphanyl, $C_1$-$C_8$-alkylsulphonyl, unsubstituted or substituted aryl, aryl-$C_0$-$C_4$-alkoxycarbonyl, cyano, halogen, unsubstituted or substituted heterocyclyl, hydroxyl, nitro, oxide, oxo, tri-$C_1$-$C_4$-alkylsilyl, trifluoromethoxy or trifluoromethyl, at least one substituent being $C_1$-$C_8$-alkylsulphanyl, hydroxyl, nitro or oxide; or (D) $R^1$ is aryl or unsaturated heterocyclyl if $R^3$ and $R^4$ are both not simultaneously deuterium or hydrogen, whereby aryl or unsaturated heterocyclyl is substituted by 1-4 $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulphonyl, unsubstituted or substituted aryl, aryl-$C_0$-$C_4$-alkoxycarbonyl, cyano, halogen, unsubstituted or substituted heterocyclyl, oxo, tri-$C_1$-$C_4$-alkylsilyl, trifluoromethoxy or trifluoromethyl; or (E) $R^1$ is aryl or unsaturated heterocyclyl if $R^2$ is $C_1$-$C_8$-alkoxy, whereby aryl or unsaturated heterocyclyl is substituted by 1-4 $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulphonyl, unsubstituted or substituted aryl, aryl-$C_0$-$C_4$-alkoxycarbonyl, cyano, halogen, unsubstituted or substituted heterocyclyl, oxo, tri-$C_1$-$C_4$-alkylsilyl, trifluoromethoxy or trifluoromethyl;

R a) is deuterium, halogen, tri-$C_1$-$C_4$-alkylsilyl, trifluoromethoxy, trifluoromethyl or hydrogen; or b) is $C_1$-$C_8$-alkoxy or $C_1$-$C_8$-alkyl;

$R^2$ a) is deuterium, halogen or hydrogen; or b) is $C_2$-$C_8$-alkenyl, $C_2$-$C_8$-alkynyl, $C_1$-$C_8$-alkoxy, $C_1$-$C_4$-alkoxycarbonyl-$C_1$-$C_4$-alkyl, $C_1$-$C_8$-alkyl, $C_0$-$C_4$-alkylcarbonyl, aryl-$C_0$-$C_4$-alkyl, carboxy-$C_1$-$C_4$-alkyl, $C_3$-$C_8$-cycloalkyl or unsaturated heterocyclyl-$C_0$-$C_4$-alkyl, which radicals may be substituted by 1-4 $C_1$-$C_8$-alkoxy, $C_1$-$C_8$-alkoxycarbonyl, $C_1$-$C_8$-alkyl, $C_0$-$C_8$-alkylcarbonyl, $C_1$-$C_8$-alkylsulphonyl, unsubstituted or substituted aryl, aryl-$C_0$-$C_4$-alkoxycarbonyl, cyano, halogen, unsubstituted or substituted heterocyclyl, hydroxyl, nitro, oxide, oxo, tri-$C_1$-$C_4$-alkylsilyl, trifluoromethoxy or trifluoro-methyl;

$R^3$ a) is deuterium, halogen, hydroxyl, trifluoromethoxy, trifluoromethyl or hydrogen; or b) is $C_1$-$C_8$-alkoxy or $C_1$-$C_8$-alkyl;

$R^4$ a) is deuterium, halogen, trifluoromethoxy, trifluoromethyl or hydrogen; or b) is $C_1$-$C_8$-alkoxy or $C_1$-$C_8$-alkyl;

n is a number 1;

and salts thereof, preferably pharmaceutically useful salts thereof, where, if $R^2$ is hydrogen $R^1$ is not carbazolyl, fluorenyl or naphthyl.

2. Compound according to claim 1, characterized in that it conforms to the general formula

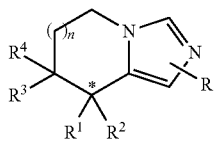 (Ia)

where the definitions of the substituents R, $R^1$, $R^2$, $R^3$, $R^4$ and n are as specified for compounds of the formula (I) according to claim 1 and * denotes an asymmetric carbon atom.

3. Compound according to claim 1 or 2, where R is $C_1$-$C_8$-alkyl, deuterium, tri-$C_1$-$C_4$-alkylsilyl or hydrogen.

4. Compound according to claim 1 or 2, where R is deuterium or hydrogen.

5. Compound according to claim 1 or 2, where $R^1$ is unsubstituted or substituted 4-acetylphenyl, 4-methanesulphonylphenyl, 4-nitrophenyl or 4-heterocyclylphenyl, the heterocycle preferably containing at least one nitrogen atom.

6. Compound according to claim 1 or 2, where $R^1$ is unsubstituted or substituted 4-heterocyclylphenyl, the heterocycle containing at least one nitrogen atom.

7. Compound according to claim 1 or 2, where $R^1$ is substituted 4-cyanophenyl or substituted 4-fluorophenyl.

8. Compound according to claim 1 or 2, where $R^1$ is benzofuran-3-yl, 1H-benzoimidazol-1-yl, benzo [d]isothiazol-3-yl, benzo[d]isoxazol-3-yl, benzo[b]thiophen-3-yl, imidazol-1-yl, indolyl, oxazol-4-yl, pyridin-4-yl, thiazol-4-yl or thiophen-3-yl, which radicals are in each case substituted.

9. Compound according to claim 1 or 2, where $R^1$ is benzofuran-3-yl, 1H-benzoimidazol-1-yl, benzo[d]isothiazol-3-yl, benzo[d]isoxazol-3-yl, benzo[b]thiophen-3-yl, imidazol-1-yl, indolyl, oxazol-4-yl, pyridin-4-yl, thiazol-4-yl or thiophen-3-yl, which radicals are in each case substituted and the substituents are selected from the group consisting of $C_1$-$C_8$-alkyl, $C_1$-$C_8$-alkoxy, $C_1$-$C_8$-alkoxycarbonyl, $C_0$-$C_8$-alkylcarbonyl, $C_1$-$C_8$-alkylsulphonyl, unsubstituted or substituted aryl, aryl-$C_0$-$C_4$-alkoxycarbonyl, halogen, cyano, unsubstituted or substituted heterocyclyl, hydroxyl, nitro, oxide, oxo, tri-$C_1$-$C_4$-alkylsilyl, trifluoromethoxy and trifluoromethyl.

10. Compound according to claim 1 or 2, where $R^2$ is hydrogen, deuterium, halogen or $C_1$-$C_8$-alkoxy and $R^4$ is hydrogen, deuterium or $C_1$-$C_8$-alkyl and in which $R^1$ is a mono-, di- or tri-substituted phenyl radical which has at least one substituent in position 4.

11. Pharmaceutical product comprising a compound of the general formula (I) according to claim 1 or 2 and conventional excipients.

12. Pharmaceutical combination in the form of a product or kit composed of individual components consisting a) of a compound of the general formula (I) according to claim 1 or 2 and b) of at least one pharmaceutical form whose active ingredient has a blood pressure-lowering, an inotropic, a metabolic or a lipid-lowering effect.

* * * * *